United States Patent [19]
Pan et al.

[11] Patent Number: 6,071,725
[45] Date of Patent: Jun. 6, 2000

[54] VECTORS EXPRESSING ICE NUCLEATION PROTEIN FUSIONS FOR CELL SURFACE ANCHORING OF FOREIGN PROTEINS

[75] Inventors: Jae Gu Pan; Heung Chae Jung; Seung Hwan Park; Moon Hi Han; Young Hoon Park, all of Taejon-si, Rep. of Korea

[73] Assignee: Korea Institute of Science and Technology, Seoul, Rep. of Korea

[21] Appl. No.: 08/973,180

[22] PCT Filed: Apr. 2, 1997

[86] PCT No.: PCT/KR97/00057

§ 371 Date: Dec. 2, 1997

§ 102(e) Date: Dec. 2, 1997

[87] PCT Pub. No.: WO97/37025

PCT Pub. Date: Oct. 9, 1997

[30] Foreign Application Priority Data

Apr. 2, 1996 [KR] Rep. of Korea ......................... 96-9921

[51] Int. Cl.[7] .............................. C12N 1/21; C12N 15/66; C12N 15/70; C12P 21/02

[52] U.S. Cl. ........................ 435/69.7; 435/69.6; 435/69.8; 435/71.1; 435/71.2; 435/476; 435/488

[58] Field of Search ................................. 435/69.1, 172.3, 435/69.7, 71.1, 71.2, 69.8, 476, 488, 69.6

[56] References Cited

FOREIGN PATENT DOCUMENTS

| 0424771 | 5/1991 | European Pat. Off. |
| 4/299985 | 10/1992 | Japan . |
| 91-7611 | 9/1991 | Rep. of Korea . |
| 89/06498 | 7/1989 | WIPO . |

OTHER PUBLICATIONS

Green et al., Mol. Gen. Genet. 215:165–172 (1988).
Microbiology, Bernard D. Davis et al., eds. Hagerstown: Harper & Row, Publishers, 1980. pp. 73, 82 and 83.

*Primary Examiner*—Johnny F. Railey, II
*Attorney, Agent, or Firm*—Dilworth & Barrese

[57] ABSTRACT

The present invention relates to surface anchoring vectors, a method for preparation of foreign proteins onto a cell surface and use thereof, which uses outer cell membrane protein, ice nucleation protein (NIP) derived from *Pseudomonas syringae*, a gram-negative bacterium.

24 Claims, 9 Drawing Sheets

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "oligonucleotide"

(xi) SEQUENCE DESCRIPTION: SEQ ID NO:1:

AAGTACAGGT ACCGCAGGTC ACGAG                                 25

(2) INFORMATION FOR SEQ ID NO:2:

(i) SEQUENCE CHARACTERISTICS:
      (A) LENGTH: 34 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "oligonucleotide"

(xi) SEQUENCE DESCRIPTION: SEQ ID NO:2:

GGAGTGCTTG AATTCCCCGG GATCCTTTAC CTCT                        34

(2) INFORMATION FOR SEQ ID NO:3:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "oligonucleotide"

(xi) SEQUENCE DESCRIPTION: SEQ ID NO:3:

GGATCCGATG TTGAATAAAG CAGGC                                 25

-continued (2) INFORMATION FOR SEQ ID NO:4:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:4:

```
GATTCCGGGA ATCAGAAACG AAACGTCA                                              28
```

VECTORS EXPRESSING ICE NUCLEATION PROTEIN FUSIONS FOR CELL SURFACE ANCHORING OF FOREIGN PROTEINS

This application is a national stage application of PCT/KR97/00057 filed on Apr. 2, 1997, which claims priority from Korean Application Ser. No. 96-9921 filed on Apr. 2, 1996.

TECHNICAL FIELD

The present invention relates to surface anchoring vectors containing gene segments of ice nucleation protein (INP), which can express foreign proteins onto a cell surface.

The present invention also relates to a method for preparing foreign proteins onto a cell surface by using INP and use of foreign proteins prepared by the surface expression system.

Particularly, the present invention relates to surface anchoring vectors, a method for preparing foreign proteins onto a cell surface and use thereof, which uses outer cell membrane proteins ice nucleation protein (INP) derived from *Pseudomonas syringae*, a gram-negative bacterium.

BACKGROUND ARTS

Presently, surface expression of proteins has been investigated in unicellular organisms such as bacteriophage, bacteria, yeast and the like to produce new vaccines, to perform screening of various antigens and antibodies and to localize useful enzymes onto a cell surface.

Surface expression of proteins has been tried at first to express antigenic peptides onto a cell surface for stable production of vaccines. Hitherto, in order to produce vaccines pathogenic bacteria were mutated arbitrarily and screened for selecting safe bacteria which can induce immunization consistently. However, the screening method has a disadvantage of losing the antigenic activities when the vaccines are administered orally into human body and animal body. Thus, many investigations have been performed to overcome the disadvantage.

First, surface expression has been performed by the process, wherein gene segments of cell surface protein were exploited in gram-negative bacteria, ligated to genes of antigenic polypeptides and used to transform proper bacteria hosts for effective production of fusion proteins. The fusion proteins prepared by the process can work as effective antigens since they are extruded onto a cell surface stably. Especially in gram-negative bacteria, outer member lipopolysaccharides (LPS) increase antigenicity of proteins expressed onto a cell surface.

To express proteins onto a cell surface, a secretion signal is necessary within primary sequences of proteins, which helps foreign proteins produced intracellularly to pass through a cell membrane. Especially in gram-negative bacteria, proteins should pass through the inner cell membrane and periplasmic space, localize onto the outer cell membrane stably and be extruded. For example, surface proteins, specific enzymes and toxin proteins have a secretion signal and a targeting signal localizing the proteins onto the cell surface. Practically, foreign proteins can be expressed on the cell surface successfully by using such a secretion signal, a targeting signal and the like combined with proper promoters.

Up to now, surface proteins present in gram-negative bacteria have been utilized mainly to produce foreign polypeptides which are necessary onto the cell surface. There are 4 kinds of proteins used for the cell surface expression, such as outer cell membrane protein, lipoprotein, secretion protein and cell surface structure protein. As outer cell membrane proteins, Lam B, Pho E, Omp A and the like have been utilized for the surface expression. In these cases, however, sizes of proteins expressed onto the cell surface are limited since the proteins should be inserted into loops extruded from the cell surface. In addition, the C- and N-termini of the foreign protein should be close to each other 3-dimensionally. Thus, when the distance between the two termini is long the C- and N-termini should be joined.

Practically, if Lam B or Pho E is utilized to insert foreign polypeptides comprising more than 50–60 amino acids, membrane proteins cannot be produced stably due to structural imitation [Charbit, et al., J. Immuol., 139: 1658–1664 (1987); Agterberg, et al., Vaccines, 8: 85–91 (1990)]. To overcome the structural limitation, a part of the Omp A protein which contains a miniumum targeting sequence localizing foreign proteins onto the outer cell membrane is used, although the whole Omp A protein was also used to insert foreign proteins into the extruded loop. By the process described about, β- lactamase was expressed onto the cell surface by fusing the C-termainal targeting sequence of Omp A protein. In this case, Omp A fragment helped proteins to be expressed and bound onto the cell surface and a signal sequence of *E. coli* lipoprotein, Lpp, which was fused to N-terminus of Omp A helped the protein to be localized onto outer cell membrane [Francisco, et al., Proc. Natl. Acad. Sci. USA, 489: 2713–2727 (1992)].

Therefore, the cell surface expression using outer membrane proteins should be performed in bacteria by the process, wherein a selected outer membrane protein fused with foreign proteins in the level of genes, is used to induce biosynthesis of fusion proteins, passes through the inner membrane stably and maintains outer membrane binding of foreign proteins. Thus, outer membrane proteins selected as a surface anchoring motif must satisfy requirements described below. The outer membrane proteins should i) have a secretion signal by which a fusion protein can pass through the inner cell membrane, ii) have a targeting signal by which the protein can bind onto the outer cell membrane, iii) be expressed massively on the cell surface and iv) be expressed stably regardless of protein size. However, any cell surface anchoring motif satisfying all the requirements has not been yet developed and only supplemented the above disadvantages.

Lipoproteins, as a surface protein, have also been used for the surface expression. Particularly, *E. coli* lipoproteins can pass through the inner cell membrane due to a secretion signal at the N-terminus and can localize directly to outer or inner membrane lipids by covalent bonding due to terminal L-cysteine. In addition, since a major lipoprotein, Lpp, binds to the outer cell membrane at the N-terminus and to the cell layer, peptidoglycan (PG), at the C-terminus, a foreign protein joined with outer membrane Omp A fragment can be secreted stably onto the outer cell membrane for the surface expression [Francisco, et al., Proc. Natl. Acad. Sci. USA, 489: 2713–2727 (1992)]. By using the characteristics of lipoproteins, another lipoprotein, Tra T, has been exploited to express peptides such as Poliovirus C3 epitope and the like onto the cell surface [Felici, et al., J. Mol. Biol., 222: 301–310 (1991)]. In addition, a peptiodoglycan-associated lipoprotein (PAL) of which the function is not known exactly has also been exploited to express recombinant antibodies on the cell surface [Fuchs, et al., Bio/Technology, 9: 1369–1372 (1991)]. In this case, PAL was joined with peptiodoglycan at the C-terminus and with the recombinant antibody at the N-terminus to express the fusion protein on the cell surface.

Secretion proteins, as a surface protein passing through the outer cell membrane, have been used for the surface expression. However, in gram-negative bacteria secretion proteins are not well-developed and only some secretion proteins participate in passing through the outer cell membrane by the proteins helping the specific secretion process. For example, a pullulanase from *Klebsiella sp.* is replaced with a lipid component at the N-terminus, binds to the outer cell membrane and is secreted into cell media. Kornacker et al., tried to express β-lactamase on the cell surface by using the N-terminal fragment of pullulanase. Unfortunately, the pullulanase-β-lactamase fusion protein bound to the cell surface instantly and was secreted into cell media. Also, alkaline phosphatase, a periplasmic space protein, was attempted to be used by the above process. But the alkaline prosphatase was not expressed stably onto the cell surface since more than 14 proteins are necessary in the secretion process [Kornacker, et al., Mol. Microl., 4: 1101–1109 (1990)].

Ig A protease is derived from a pathogenic microorganism, Neisseria and has a unique secretion mechanism. The C-terminal β-fragment of Ig A protease has a signal by which the N-terminal protease can be localized onto the outer cell membrane. After the protease reaches the outer cell membrane to be extruded on the cell surface, the extruded protease is secreted into cell media by auto-hydrolysis. By using the β-fragment of the Ig A protease, Klauser et al. also expressed 12 kDa chloera toxin B subunit stably onto the cell surface [Klauser, et al., EMBO J., 9: 1991–1999 (1990)]. However, secretion of the fusion protein was inhibited since a protein folding is induced in the periplasmic space during the secretion process.

In addition, other cell surface structures which are present on cell surface, such as flagella, pili, fimbriae and the like, can be used for the surface expression. By using flagellin, a structural subunit of flagella, respective chlolela toxin B subunit and other peptides derived from Hepatitis B Virus were expressed stably and these peptides could bind with the respective antibody intensively [Newton, et al., Science, 244: 70–72 (1989)]. By using fimbrin, a structural protein of fimbriae which works on cell surface like threads, foreign proteins were also expressed. As a result, only small peptides have been expressed successfully [Hedegaard, et al., Gene, 85: 115–124 (1989)].

In addition to the surface proteins of gram-negative bacteria, those of gram-positive bacteria has been attempted to express foreign proteins on cell surface recently [Samuelson, et al., J Bacteriol., 177: 1470–1476 (1995)]. Also, a surface anchoring motif passing through the inner cell membrane and binding to the cell membrane is necessary. Practically a secretion signal of lipase derived from *Staphylococcus hyicus* and a membrane-bound matrix of protein A derived from *Staphylococcus aureus* sere used to express foreign proteins onto the cell surface. As a result, a malaria blood state antigen comprising 80 amino acids and an albumin binding protein derived from G protein of Streptococcus were expressed on the cell surface of gram-positive bacteria efficiently.

In investigating the surface expression in gram-negative and gram-positive bacteria as described above, useful systems for the protein expression have been developed a lot. For recent 3 years, the systems have been filed and registered as patent rights in USA, Europe, Japan and the like. In particular, 5 cases using the outer cell membrane of gram-negative bacteria were registered Also, 1 case using a pilus, a cell surface structure, and 1 case using a cell surface lipoprotein were registered.

The inventors have exploited ice nucleation protein (INP), a surface protein derived from *Pseudomonas syringae* KCTC 1832, as a new surface anchoring motif and developed new surface anchoring vectors containing INP for expressing foreign proteins efficiently on a cell surface, a method for preparation of foreign proteins onto a cell surface and use thereof.

SUMMARY OF THE INVENTION

The object of the present invention is to provide surface anchoring vectors for the surface expression exploiting characteristics of ice nucleation protein (INP). Particularly the vectors of the present invention contain a secretion signal and a targeting signal which INP has in its primary sequence.

Another object of the present invention is to provide a method for preparing foreign proteins, which uses the surface anchoring vector using characteristics of INP and expresses foreign proteins onto a cell surface.

Particularly, the present invention provides a method for preparing foreign proteins, wherein proteins are utilized conveniently even without cell disruption or isolation since the proteins are expressed onto the surface.

In addition, the present invention can provide uses of foreign proteins expressed onto a cell surface, which comprises effective production of antibodies and antigens and production of libraries for screening antigens, binding or adsorbent proteins, physiological activators and the like. For example levansucrase expressed onto the cell surface can be utilized to produce levan efficiently.

All the surface anchoring vectors containing INP gene derived from *Pseudomonas syringae* KCTC 1832 can be within the scope of the present invention.

And the surface anchoring vectors of the present invention can be applied to all the bacteria hosts. Preferably the host can be selected among gram-negative bacteria and more preferably among *Escherichia coli,* Acetobacter sp., Pseudomonas sp., Xanthomonas sp., Erwinia sp. and Kymomonas sp.

All of the methods for the preparation using these bacteria can be within the scope of the present invention.

In particular embodiments, the pANC3 vector (accession number: KCTC 0326 BP) has been constructed, wherein central repeating domain-deleted INP gene derived from *Pseudomonas syringae* KCTC 1832 is contained and foreign genes can be easily cloned due to C-terminal restriction site inserted.

In addition, all or some restriction sites can be inserted into the C-terminus of INP and all the surface anchoring vectors containing these restriction sites can be within the scope of the present invention.

In particular embodiments, the pANC3-CM2 recombinant vector has been constructed, wherein a central repeating domain-deleted INP gene is contained and at the C-terminus of the INP gene the N-terminus of CMCase gene is ligated to produce CMCase onto a cell surface in the form of a fusion protein.

In particular embodiments, the pGINP21M vector (accession number: KCTC 0239 BP) has been constructed, wherein INP gene is contained and foreign genes can be easily cloned due to C-terminal restriction site inserted.

And in particular embodiments, the pASCM1 recombinant vector (accession number: KCTC 0237 BP) has been constructed, wherein INP gene is contained and at the C-terminus of INP gene the N-terminus of carboxymethylcellulase (CMCase) gene is ligated to produce the CMCase onto a cell surface in the form of a fusion protein And in particular embodiments, the pASLP1 recombinant vector has been constructed, wherein INP gene is also contained and at the C-terminus of INP gene the N-terminus of a lipase gene is ligated instead of CMCase gene to produce lipase onto a cell surface in the form of a fusion protein.

And in particular embodiments, the pASIg1 recombinant vector has been constructed, wherein INP gene is also contained and at the C-terminus of INP gene the N-terminus of single chain Fv antibody gene is ligated instead of the CMCase gene to produce single chain Fv antibody onto a cell surface in the form of a fusion protein.

An in particular embodiments, the pSSTS109 recombinant vector has been constructed, wherein INP gene is also contained and levansucrase gene is ligated to produce levansucrease onto a cell surface in the form of a fusion protein.

DETAILED DESCRIPTION OF THE PREFERRED EMBODIMENTS

Ice nucleation protein, a outer cell membrane protein, is formed in *Pseudomonas sp., Erwinia sp., Xanthomonas sp.* and the like and has a unique function which induces ice formation in supercooled water.

Considering the sequences of INP genes form various kinds of bacteria, especially 8 amino acid units are repeated in the central region of INP. The unit is expected to provide a frame arranging the supercooled water like ice particles. An specific amino acid sequences are present at the N- and C-termini of INP respectively. The sequences are expected to be a secretion signal and a targeting signal by which INP can pass through the inner cell membrane. Especially, the N-terminus of INP plays a role in binding onto the outer cell membrane.

INP is composed of more than 1,200 amino acids and its molecular weight is 118 kDa. The primary amino acid sequence is composed of the N-terminal unique amino acids (15% of the total protein sequence), the C-terminal unique amino acids (4% of the total protein sequence) and the central repeating domain (81% of the total protein sequence). Especially, 8 amino acid units are repeated exactly 122 times within the central region of INP.

Green et al. has investigated physiological functions of INP by using mutants of INP gene in 3 respective regions of the protein [Green, et al., Mol. Gen. Genet., 215: 165–172 (1988)]. As a result, the length of the central repeating units of INP is identified to affect ice nucleation activity. Lack of the repeating property reduces or loses the ice nucleation activity and only decrease in the length of the central region maintains the ice nucleation activity. Therefore, the repeating region is expected to arrange supercooled water molecules adjacent to INP for the formation of the ice particle structure regardless of protein secretion and targeting. An the N-terminus of INP is expected to play a role in binding onto the outer cell membrane. The ice nucleation activity is maintained even when the N-terminus of INP is cleaved completely. However, the C-terminal of INP is expected to play a role in secreting and targeting INP onto the outer cell membrane. The ice nucleation activity reduces completely due to C-terminal cleavage.

As a surface expression matrix, INP has many advantages derived from it primary amino acid sequence, its structure and its characteristics. First, INPs are expressed massively onto the cell surface. Second, INP expressed onto the cell surface is maintained stably in the stationary phase of cell growth. Third, INP resides are on the outer cell membrane and exposed to the external surface. Fourth, the distance between foreign protein and cell surface can be adjusted conveniently since the length of the central repeating unit of INP can be flexible according to sizes of foreign proteins. Fifth, since INP is a stable enzyme expressed in a broad range of gram-negative bacteria, various hosts of gram-negative bacteria can be exploited for the surface expression.

Figure 1:
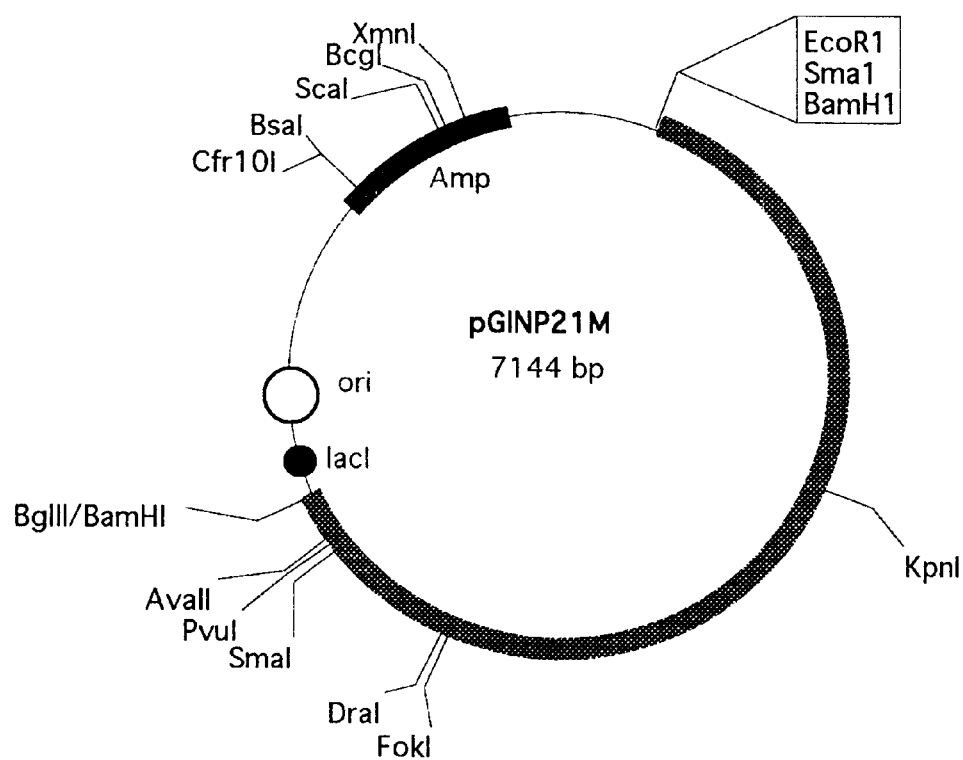
FIG. 1 shows a restriction map of the pGINP21M vector which contains INP gene and some restriction sites at the C-terminus of INP gene.

To construct the surface anchoring vector containing INP gene, the pGINP21 (accession number: KCTC 86089) plasmid containing required genes has been used. At the C-terminus of INP a translation termination codon is excised and 3 new restriction sites, such as Bam HI, Sma I and Eco RI, are inserted by the polymerase chain reaction (PCR), which provides insertion sites for foreign protein genes. As a result, the pGINP21M vector (accession number: KCTC 0239 Bp) is constructed (see FIG. 1), wherein any restriction enzyme site mentioned above is available to insert foreign protein genes by gene manipulation framing the translation codon.

In addition, various vectors containing all or some restriction sites at the C-terminus of INP can be constructed.

The surface anchoring vector constructed by the above process contains the original INP DNA sequence and expresses INP. And when foreign protein genes are ligated at the C-terminus of INP in frame, fusion proteins can be expressed and bound stably onto the cell surface.

For effectiveness of the surface anchoring vector, it should be identified that foreign proteins be synthesized, pass through inner cell membrane and be bound onto the cell surface. Thus, foreign protein genes are ligated to INP gene in frame, transforms bacteria hosts to induce for expression and the fusion protein is identified to be expressed onto cell surface.

By using the pGINP21M vector constructed by the above process, the pASCM1 recombinant vector (accession number: KCTC 0237 BP) has been constructed to express carboxymethylcellulase (CMCase) derived from a gram-negative bacterium, Bacillus sp. onto cell surface. The N-terminal 360 bp DNA of carboxymethylcellulase gene is obtained from the pUC19 vector containing the gene [Park, et al., Enzyme Microb. Technol., 8(12): 725–738 (1986)] and inserted into the pGINP21M vector. Then the C-terminal DNA fragment of CMCase if obtained from the different pUC19 vector and inserted into the vector prepared above to construct the pASCM1 recombinant vector (see FIG. 2.)

Figure 3:
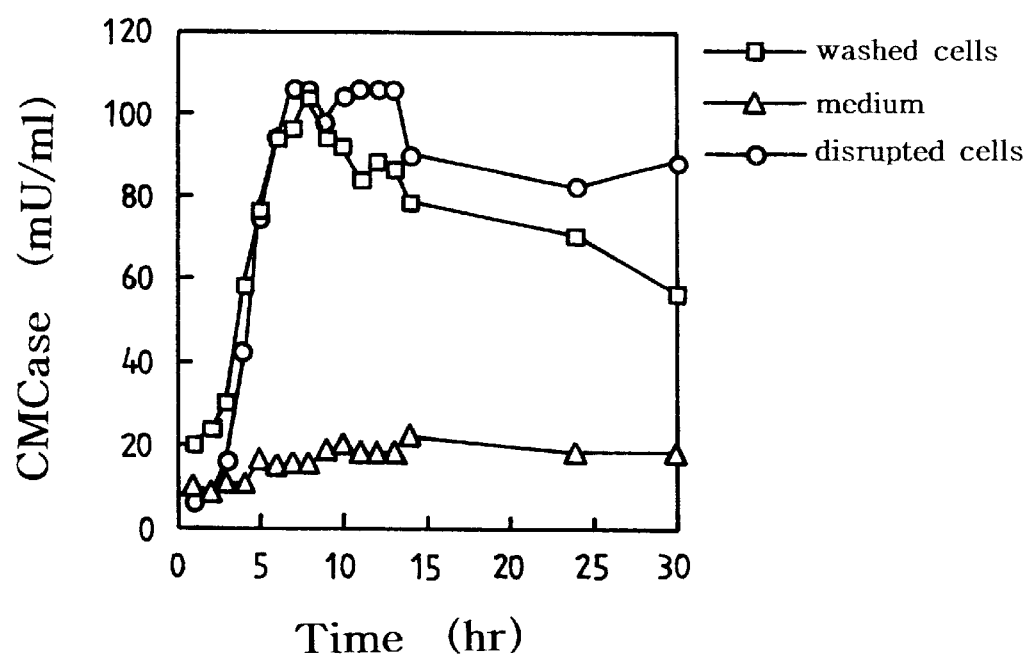
FIG. 3 illustrates activities of CMCase expressed onto the cell surface from *E. coli* transformant of the pASCM1 recombinant vector with the graph, which compares the activities in washed cells, medium and disrupted cells respectively.

To express CMCase enzyme onto the cell surface, E. coli is transformed with the pASCM1 recombinant vector, cultured and induced for the surface expression. Then, the CMCase activity is measured by using carboxymethylcellulose as a substrate. As a result, the enzyme activities of the present invention are similar in washed whole E. coli cells and disrupted E. coli cells respectively. Hence, it is expected that the total enzyme activity appears only in a CMCase extruded onto the cell surface. Since carboxymethylcellulose has too high a molecular weight to penetrate the outer cell membrane, the enzyme activity can appear by the process, wherein the cell surface expressing CMCase in contact with a carboxymethylcellulose dissolved in substrate solution. Since cell medium does not show the CNCase activity it is suggested that CMCase be seldom separated from the cell surface and limit the enzyme activity (see FIG. 3.).

The pASLP1 recombinant vector containing INP has been constructed to express lipase derived from a gram-negative bacterium, Pseudomonas sp., onto the cell surface. The lipase gene is obtained from the pJH92 plasmid (Jung, Kook Hoon, Department of Biological Science, Ph D Thesis, KIST, 1990) by performing PCR and ligated with the pASCM1 recombinant vector digested with BAM HI and Eco RI to construct toe pASLP1 recombinant vector producing the fusion protein of INP and lipase.

To express the lipase onto the cell surface, E. coli is transformed with the pASLP1 recombinant vector, cultured and induced for the surface expression. Then, the lipase activity is measured by the cupuric acetate method. Compared with host cells lacking lipase, the higher lipase activity appears in transformed E. coli expressing lipase onto the cell surface. Therefore the host cells expressing lipase onto the cell surface can be utilized directly in double-phase lipolysis (see the FIG. 4.).

The pASIg1 recombinant vector containing INP gene has also constructed to express a single chain Fv antibody. The single chain Fv antibody gene is obtained from the pLUV2 plasmid which can produce the antibody as a secretion protein in E. coli and inserted by the process described above to construct the pASIg1 recombinant vector.

To express the single chain Fv antibody onto the cell surface, E. coli is transformed, cultured and induced for the surface expression. Then, the surface expression of the single chain Fv antibody is identified by the ELISA (Enzyme-linked Immunoassay) method which measures degrees of antigens binding with surface-expressed antibodies.

And the pSSTS109 recombinant vector (accession number: KCTC 0327 BP) containing INP gene has been constructed to express levansucrase. The leansucrase gene is obtained by performing PCR with the pZL8 vector, subcloned into the pT7Blue(R) vector and then inserted into the pGINP21M vector of the present invention.

To express levansucrase onto the cell surface, E. coli is transformed, cultured and induced for the surface expression. The surface expression of levansucrase is observed by performing immunofluorescence staining (see FIG. 8.).

Figure 9:
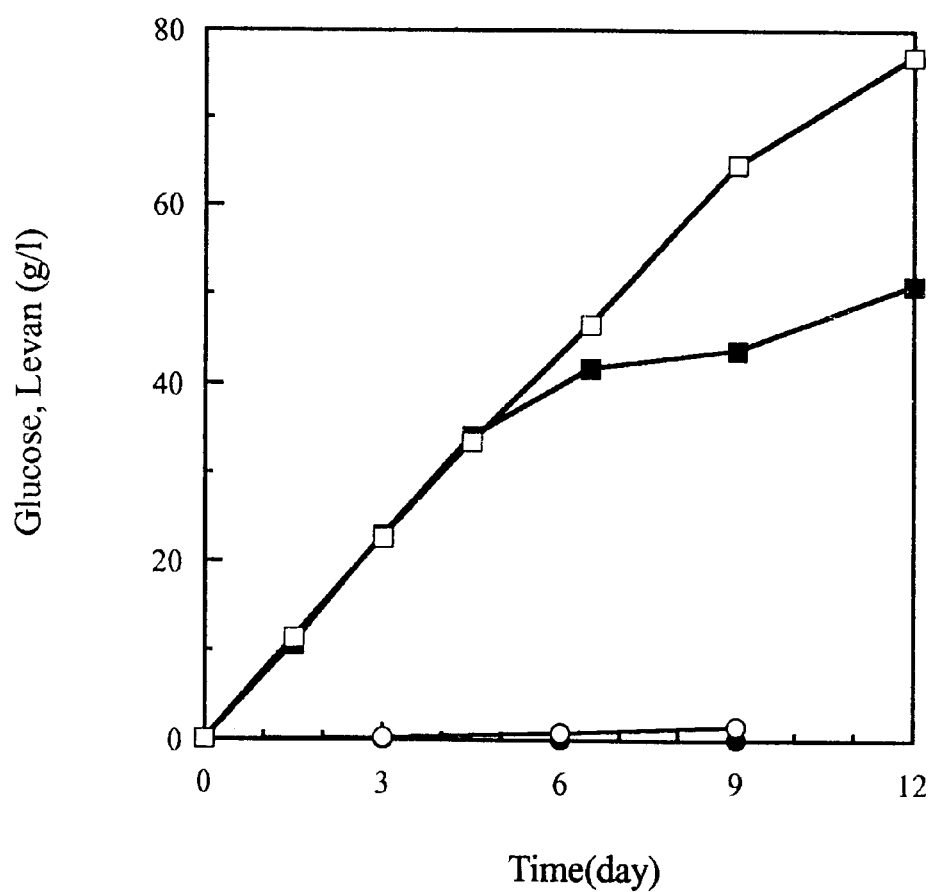
FIG. 9 shows bioconversion of sucrose to levan in whole cell system wherein *E. coli* DH5α transformant of the pSSTS109 recombinant vector is utilized.

In addition, levansucrase expressed onto the cell surface can be used to produce levan from sucrose conveniently and efficiently (see FIG. 9.).

To construct the surface anchoring vector containing repeating domain-deleted INP gene INP gene has been mutagenized to delete the central repeating domain.

Precisely gene segments encoding the N-terminal specific domain, the first 2 repeating subunits, the last 3 repeating subunits and the C-terminal specific domain of INP are cloned under the tac promoter of the pKK223-3 plasmid vector. As a result the pANC3 vector (accession number: KCTC 0326 BP) is constructed (see the FIG. 6).

By using the pANC3 vector constructed by the above process the pANC3-CM2 recombinant vector has been constructed to express CMCase onto cell surface. The CMCase activity was measured by the process described above (see FIG. 7.).

As described above, the surface expression system of the present invention has produced useful enzymes and antibodies efficiently. The foreign proteins expressed above as examples illustrate the surface expression by using INP, which by no means limits the present invention. Any foreign protein can be expressed onto a cell surface by cell surface expression system of the present invention.

The following examples will further illustrate the present invention, which by no means limits the present invention.

EXAMPLES

Example 1

Construction of the pGINP21M vector for the surface expression.

To construct the surface anchoring vector containing INP gene, the pGINP21 plasmid (71 kb) containing INP gene cloned was used (deposit authority: Korea Research Institute of Bioscience and Biotechnology; (@52, Oun-dong, Yusong-Ku, Taejon 305–600, Republic of Korea) accession number: KCTC 86089, accession date: Jul. 13, 1994). To provide insertion sites of foreign protein genes, 3 new restriction sites were inserted by PCR reaction. As a result, about 1.7 kb fragment which ranges from Kpn I site to the C-terminus of INP gene was amplified by PCR machine.

A SEQ. ID. No. 1 primer and a SEQ. ID. No. 2 primer were used. The SEQ. ID. No. 1 primer was synthesized to insert a Kpn I restriction site and the SEQ. ID. No. 2 primer was synthesized to insert 3 restriction sites such as Bam HI, Sam I and Eco RI sequentially. The restriction sites inserted facilitated the subcloning of INP gene after gene amplification. The gene fragment amplified by PCR machine was digested with restriction enzymes, Kpn I and Eco RI, and inserted into the pGINP21vector already digested with Kpn I and Eco RI. As a result, the pGINP21M vector was constructed (see the FIG. 1.), wherein new restriction sites are inserted instead of translation termination codon of INP gene. The size of the pGINP21M vector is 7.1kb. E. coli was transformed wit the pGINP21M vector of this invention and the transformed *E. coli* has been deposited with KRIBB. KIST on Mar. 28, 1996 (accession number: KCTC 0239 BP).

Example 2
Construction of the pASCM1 recombinant vector.

The pASCM1 recombinant vector was constructed, which uses INP and can express CMCase on the cell surface.

Figure 2:
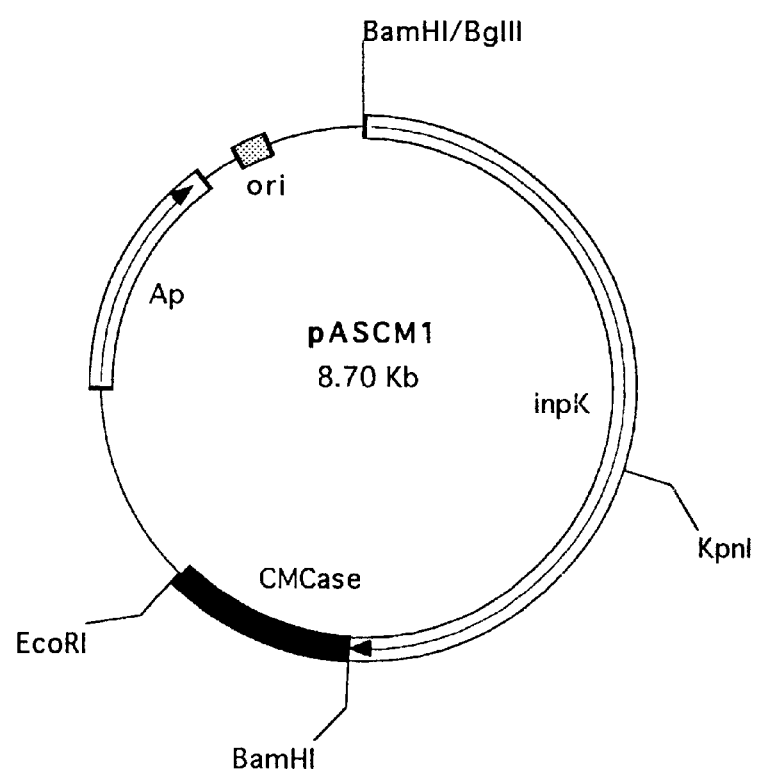
FIG. 2 shows a restriction map of the pASCM1 recombinant vector contains CMCase gene and expresses CMCase onto cell surface.

To insert CMCase gene into the pGINP21M vector for the surface expression, the vector was digested with Bam HI and Eco RI and pUC19 universal cloning vector containing the N-terminal 360 bp DNA of CMCase was also digested with Bam HI and Eco RI. Two DNA fragments prepared above were joined with DNA ligase to construct the pGINP21CM1plasmid. Then, the C-terminal DNA fragment of CMCase was obtained from Eco RI sites of another pUC19 vector by digesting with Eco RI and inserted into Eco RI site of the pGINP21CM1plasmid containing the N-terminus of CMCase. As a result, complete CMCase gene was joined to the C-terminus of INP gene. The pASCM1 recombinant vector prepared above is shown in FIG. 2. *E. coli* was transformed wit the pASCM1 recombinant vector of this invention and the transformed *E. coli* has been deposited with KRIBB, KIST on Mar. 22, 1996 (accession number: KCTC 0237 BP).

Example 3
Surface expression of CMCase

*E. coli* was transformed with the pASCM1 recombinant vector, cultured in 500 ml flask containing 100 ml of LB medium and antibiotics, 100 mg/L ampicillin, and induced for the surface expression.

Then, CMCase activity was measured by DNS method using carboxymethylcellulose as a substrate. In particular, 1%(w/v) carboxymethylcellulose was dissolved in 50 mM citrate buffer to prepare the substrate solution. 0.5 ml of this substrate solution was added, mixed well with 0.5 ml of the enzyme solution and warmed up in a double boiler at 60° C. for 30 minutes for reaction. Then, 3 ml of DNS solution was added, which had been prepared by dissolving 7.5 g of 2,5-dinitrosalicylic acid, 14.0 g of NaOH, 216.1 g of Rochel salt, 5.4 g of phenol and 5.9 g of $Na_2S_2O_5$ sequentially in 1 L of pure water. The substrate solution was reaction with DNS solution in boiling water for 5 minutes and then cooled in ice water. Using the cooled solution of room temperature, absorbance at 550 nm was measured and the amount of reducing sugar released was calculated by comparing with a standard curve of glucose. Enzyme 1 unit indicates the amount of enzyme which releases 1 $\mu$M glucose for 1 minute.

As a result, when washed whole *E. coli* cells and disrupted *E. coli* cells were used as enzyme sources the enzyme activities of both cases are similar.

Example 4
Construction of the pASLP1 recombinant vector.

The pASLP1 recombinant vector was constructed, which uses INP and can express lipase on cell surface.

The pASCM1 recombinant vector prepared in Example 2 was digested with Bam HI and Eco RI and CMCase gene was removed to prepare the surface anchoring vector. To obtain a lipase gene, the pJH92 plasmid containing this gene was used and manipulated to insert Bam HI and Eco RI restriction sites by PCR technique. Thus, the lipase gene can be obtained by digesting this pJH92 vector with Bam HI and Eco RI and was ligated into the surface anchoring vector prepared above. As a result, the pASLP1 recombinant vector was constructed, which can express INP and the lipase in the form of fusion protein.

Example 5
Surface expression of lipase.

Figure 4:
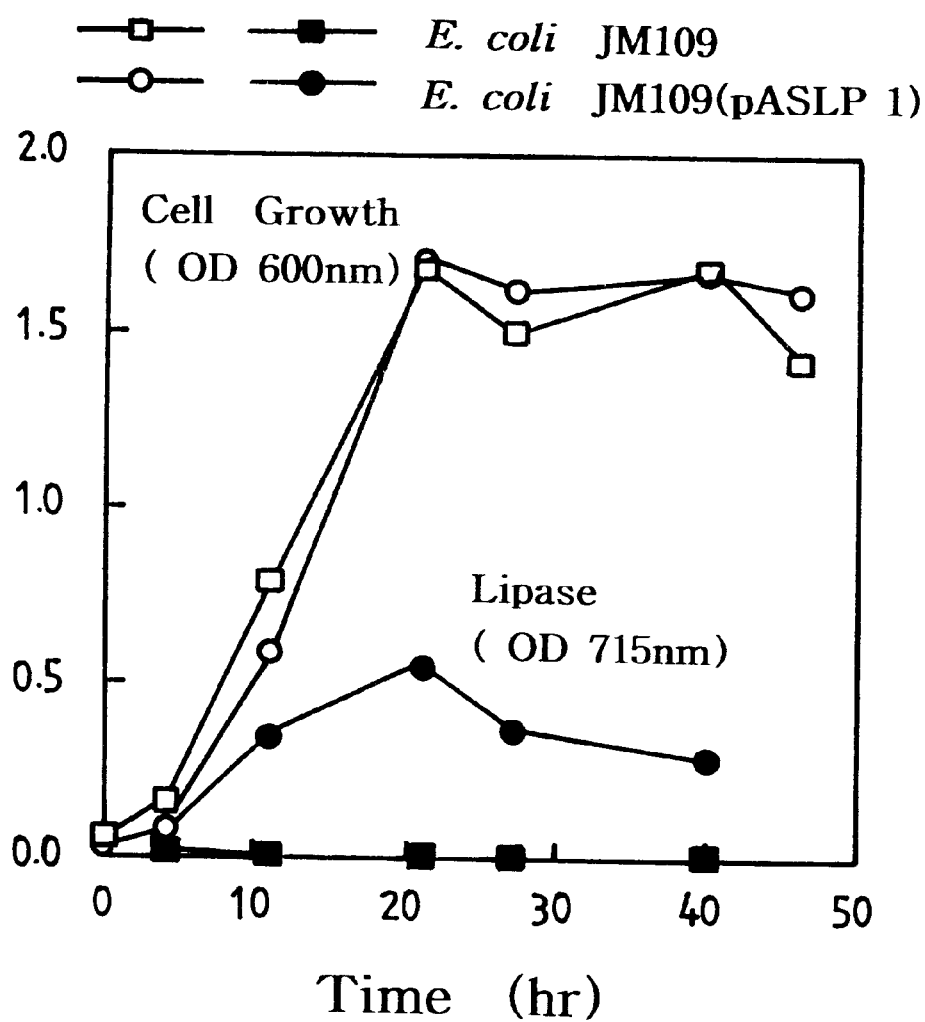
FIG. 4 illustrates activities of lipase expressed onto the cell surface from *E. coli* transformant of the pASLP1 recombinant vector by the degrees of lipolysis.

*E. coli* was transformed with the pASLP1 recombinant vector by the calcium chloride method, cultured by the same method as described in Example 3 and induced for the surface expression. Then, the lipase activity expressed onto the cell surface was measured by the Cupric acetate method as described below. 5 ml of *E. coli* culture fluid was mixed with 5% of olive oil substrate dissolved in 5 ml of iso-octane and was reacted at 40° C. for 1 hr. Then, the phase of solution and oil were suspended and 3 ml of the suspended solution was treated with 1 ml of the cupuric acetate reagent by shaking vigorously. Then, the absorbance at 715 nm of the reaction mixture was measured. At that time it is expected that the higher the absorbance, the higher the enzyme activity since much oil was degraded to produce acidic lipid. As a result, the lipase activity expressed onto the cell surface was measured as indicated in FIG. 4.

Example 6
Construction of the pASIg1 recombinant vector.

The pASIg1 recombinant vector was constructed, which uses INP and can express the humanized single chain Fv antibody onto the cell surface.

To prepare the single chain Fv antibody gene, the pLUV2 plasmid which contains the single chain Fv antibody gene and can produce this antibody as a secretion protein, was digested with Sal I and Eco RI and ligated a synthetic oligonucleotide to add a new Bgl II restriction site instead of a Sal I site. The pASCM1 recombinant vector prepared in Example 2 was digested with Eco RI and Bam HI to remove CMCase gene for the surface expression and ligated to the single chain antibody gene digested with Bgl II and Eco RI. As a result, the pASI1 recombinant vector was constructed, which can express INP and the single chain Fv antibody in the form of a fusion protein.

Example 7
Surface expression of single chain Fv antibody.

*E. coli* was transformed with the pASIg1 recombinant vector and induced by the same method as described in Example 3 for the surface expression. Then, the activity of single chain Fv antibody expressed onto the cell surface was identified by ELISA method which measures degrees of antigens binding with surface-expressed antibodies. In cells expressing antibodies and cells containing only the expression vector, the degrees of antigen-binding were compared respectively.

The respective cells were adjusted to have the same concentrations, harvested, washed with PBS buffer (pH 7.4) and resuspended with 1.4 ml of the same buffer. These suspension solution were divided into 25, 50, 100, 200 and 250 $\mu$l batches, then mixed with pre-S2 antigens of the critical concentration which an bind antibody (H69k) and reacted for 2 hours at room temperature. Then the binding solution was centrifuged for 2 minutes at room temperature and the resulting supernatant was added into ELISA plates to coat overnight. At that time, calculated amounts of the antibody, H69k, were added and amounts of the coated antibodies were measured by the ELISA method as follows.

Figure 5:
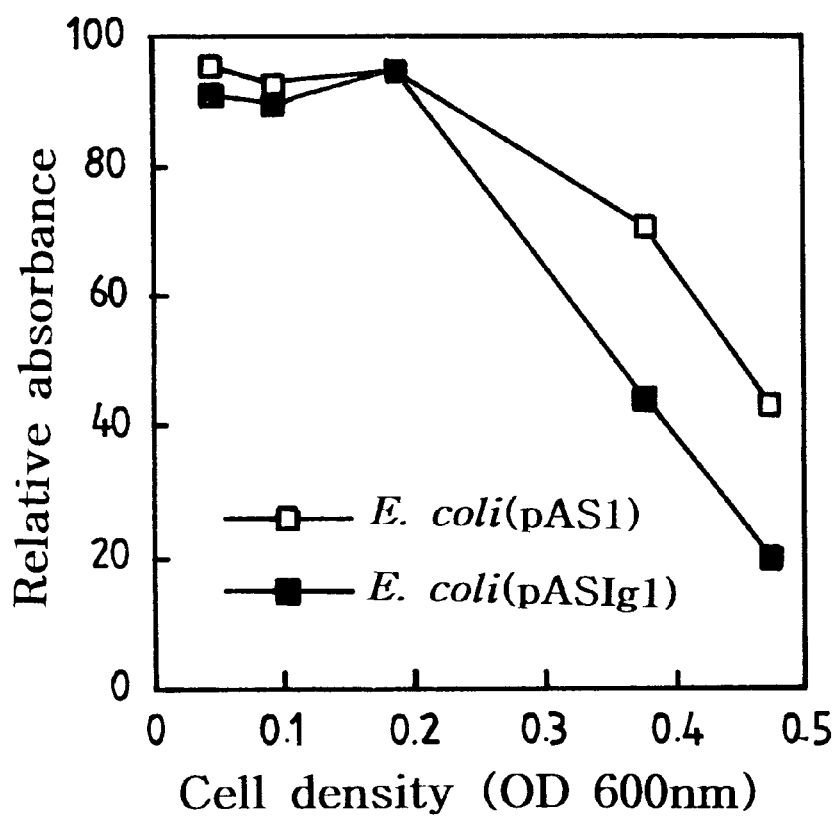
FIG. 5 illustrates binding activities of single chain Fv antibody expressed onto the cell surface from *E. coli* transformant of the pASIg1 recombinant vector with antigens by performing ELISA method.

The overnight coated plates were blocked for 2 hours by using TBS-T buffer [0.05% (v/v) Tween-20, 10 mM Tris, pH 7.4, 0.15 M NaCl] containing 2% bovine serum albumin and washed with TBS-T buffer. Then, 10 ng of the primary antibody, H69k, was added, reacted for 2 hours and washed with the same buffer to remove unbound antibodies. The secondary antibody bound with horse-radish peroxidase was diluted with 1000 times of the buffer and reacted. $H_2O_2$ as a substrate of peoxidase and OPD as a coloring reagent were added to induce coloring and this reaction was stopped by using suphuric acid. Then, absorbance at 492 nm was measured and coverted into percentages against 100% of the absorbance of the blank which does not contain cells. As a result, Antigen-binding was compared with that of control cells as indicated in FIG. 5.

Example 8

Construction of the pSSTS109 recombinant vector containing levansucrase gene

The pSSTS109 recombinant vector was constructed, which uses INP and can express levansucrase onto the cell surface.

Precisely levansucrace gene was inserted into the pGINP21M vector of the present invention. The pZL8 vector [Song and Rhee, Biotechnol. Lett., 16: 1305–1310 (1994)] was used as a template to perform PCR for amplification of leavansucrase gene. At that time oligonucleotides of SEQ. ID. No. 3 and SEQ. ID. No. 4 complementary to upstream and downstream sequences of open-reading frame (ORF) respectively, and containing new restriction enzyme sites, Bam HI site at the beginning and Sma I and Eco RI sites at the end of ORF were used as primers. The PCR products were subcloned efficiently in to the pT7Blue(R) vector (Novagen Co., USA). The subcloned levansucrase gene was digested with Bam HI-Eco RI and inserted into the pGINP21M vector digested wit the same enzyme.

As a result, the pSSTS109 recombinant vector was prepared, *E. coli* DH5α was transformed and the transformed *E. coli* has been deposited with KRIBB, KIST on Mar. 27, 1997 (accession number: KCTC 0327 BP).

Example 9

Surface expression of levansurcrase

*E. coli* were transformed with the pSSTS109 recombinant vector and induced by the same method as described in Example 3 for the surface expression.

Figure 8:
FIG. 8A–D shows immunofluorescence staining of *E. coli* DH5α transformant of the pSSTS109 recombinant vector. Left panels (A and C) show light microscopic images of *E. coli* transformant of the pZL8 vector and that of the pSSTS109 recombinant vector and right panels (B and D) show confocal fluorescent microscopic images of above *E. coli* tranformants respectively.
Figure 8:
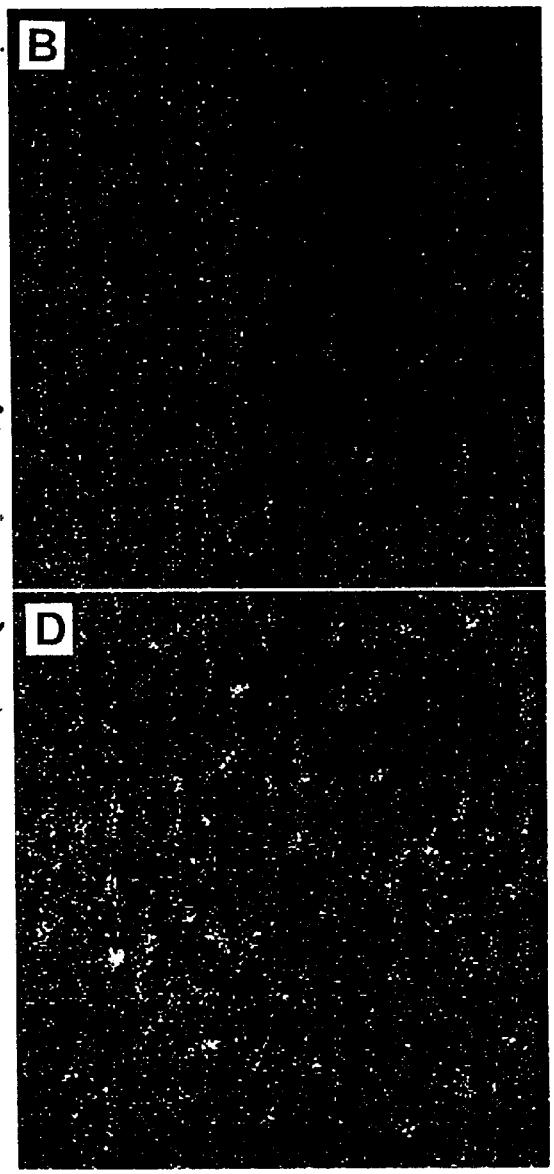

The physical observation of the surface anchored levansucrase is presented in FIG. 8. This levansucrase was stained with immunofluorescence of levansucrase-reacting antibody and FITC-labelled secondary antibody. The positive reacting cells were stained efficiently as shown in FIG. 8(D), whereas the negative reacting cells were not stained (see FIG. 8(B)). This is a direct evidence that INP can direct foreign proteins onto outer cell membrance and be useful as a surface anchoring motif.

Example 10

Bioconversion of sucrose to levan by using the surface expression system

Enzymatic conversion of sucrose to levan by using levansucrase was reported [Song and Rhee, Biotechnol. Lett., 16: 1305–1310 (1994)]. The optimal temperature of the bioconversion was 10° C. with the highest yield of 46% in 10% sucrose solution. Whole cells expressing levansucrase on their surface by using INP anchoring motif was washed and then used for direct formation of levan with a maximum yield without isolation of enzymes or making cell lysate if they were resuspended in sucrose solution buffered with acetate (pH 5.5) at 10° C. (see FIG. 9).

Initially cell concentration was low such as 1.3 $OD_{600nm}$. Because specific activity of levansucrase was high enough, this cell density was proper to apply for bioconversion. Precisely 77% of sucrose added was hydrolyzed and polymerized to levan (51.1g/l) during 12 days of the reaction. At that time unpolymerized glucose was liberated from the above sucrose solution and accumulated (77g/l). Compared with the result of this the positive cells, the negative cells which harbored levansucrase in the cytoplasmic space could not convert sucrose to levan during the reactions. As a result, only a small amount of glucose was detected such as 2.13g/l with unmeasurable amount of levan. Thus it is confirmed that levan formation with washed whole cells resulted from the reaction of surface exposed levansucrase.

Example 11

Construction of the pANC3 vector, containing repeating donan-deleted INP.

In order to construct the surface anchoring vector containing repeating domain-deleted INP gene has been mutagenized to delete the central repeating domain.

Figure 6:
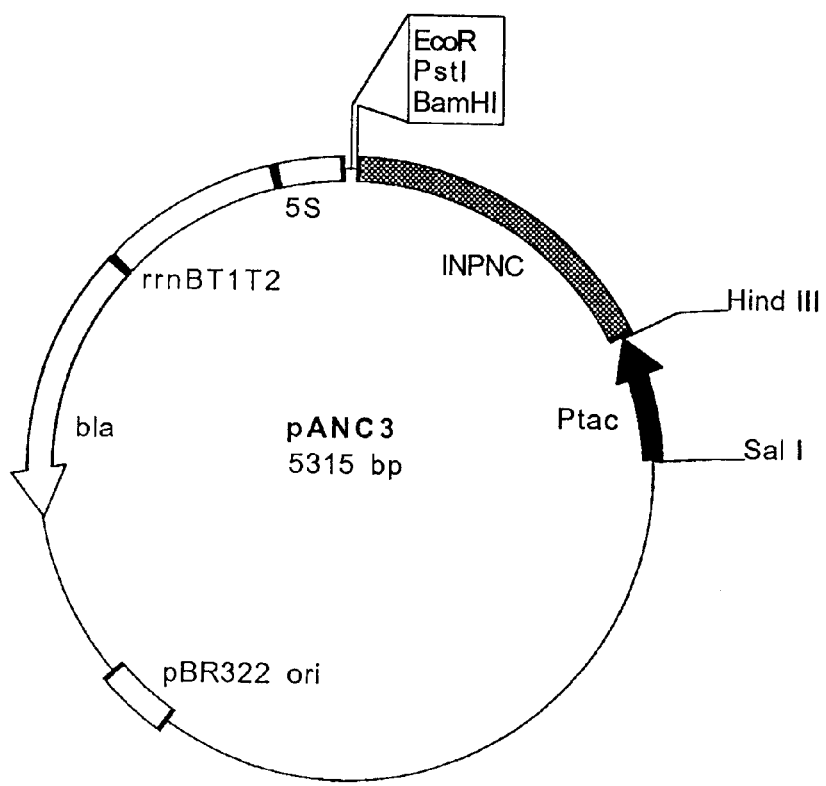
FIG. 6 shows a restriction map of the pANC3 vector which contains repeating domain-deleted INP gene.

Precisely the recombinant DNA encoding the N-terminal specific domain of INP (175 amino acid residues), the first 2 repeating subunits (32 amino acid residues), the last 3 repeating subunits (48 amino acid residues), and the C-terminal specific domain of INP (49 amino acid residues) were placed under the tac promoter of the PKK223-3 plasmid vector (Pharmacia Co., Sweden), resulting in the surface anchoring vector, pANC3, (see FIG. 6.).

*E. coli* was transformed wit the pANC3 vector of this invention and the transformed *E. coli* has been deposited with KRIBB, KIST on Mar. 27, 1997 (accession number: KCTC 0326 BP).

Example 12

Construction of the pANC3-CM2 recombinant vector

The pANC3-CM3 recombinant vector was constructed, which uses repeating domain-deleted INP and can express CMCase on the cell surface.

Precisely CMCase gene was also subcloned into the pANC3 vector to prepare the surface anchoring vector, pANC3-CM2, by performing the same procedure of Example 2.

Example 13

Surface expression of CMCase with repeating domain-deleted INP

INP is a large polypeptide with the internal repeating domain which may not be necessary to be transported onto outer cell membrane. CMCase gene was also subcloned into the pANC3 anchoring vector, preparing the pANC3-CM2recombinant vector as described in Example 12. *E. coli* JM109 strain was transformed wit the pANC3-CM2 recombinant vector and whole CMCase activity on the cell surface of the transformed *E. coli* JM109 was determined by performing the same procedure of Example 3.

Figure 7:
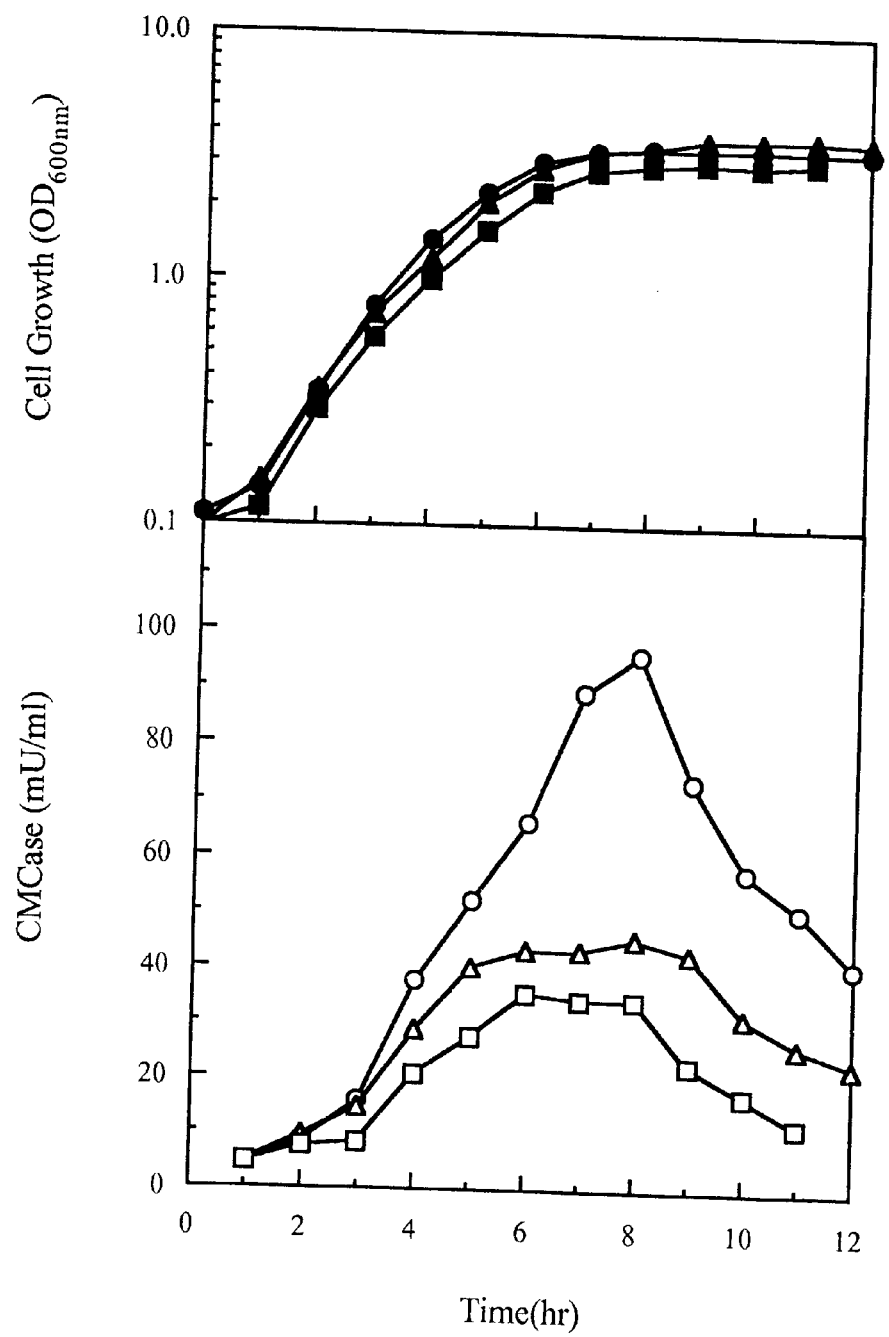
FIG. 7 illustrates activities of CMCase expressed onto the cell surface from *E. coli* transformant of the pANC3-CM2 recombinant vector.

It was confirmed by measuring whole cell CMCase activity after washing the cells (see the FIG. 7). The cells grown at 42° C. indicated higher level of CMCase activity than the cells grown at 37° C. Its activity reached maximum point at early stationary phase of growth, and then the activity decreased for several hours.

The results demonstrate that the N-terminal and/or C-terminal domain of INP may have secretion and targeting signals on its own primary sequence because INP lacking the central repeating domain of INP also directs CMCase on the cell surface.

The pGINP21M vector and the pANC3 vector prepared in the present invention have expressed CMCase, a lipase, a humanized single chain Fv antibody, levansucrase and the like onto the cell surface of *E. coli* efficiently. This vector is very advantageous as described below. The proteins expressed are not diluted due to proteins concentration onto the cell surface. The expression can be identified easily only by washing the cells since cell disruption or protein isolation or purification is not necessary.

The vector of the present invention using the characteristics of INP is useful to clone foreign protein genes since the length of the central repeating region of INP, excepting a secretion signal and a targeting signal in the primary sequence of INP, can be flexible according to needs. Thus, this vector has a outstanding advantage that the distance between the foreign protein and the cell surface can be adjusted conveniently.

The method for the preparation of the present invention uses the characteristics of INP and can express foreign proteins stably regardless of the cell cycle. It can be applied to various kinds of the bacteria hosts. In addition, the surface expression facilitates the identification of foreign proteins on account of massive expression onto the cell surface.

The surface expression system of the present invention can be used to produce recombinant foreign proteins efficiently, which comprises various antigens, antibodies, enzymes, binding or adsorbent proteins, peptide libraries for screening physiological activators and the like. Since this system has a broad range of applications, it can be used to produce new vaccines, anti-peptide antibodies, adsorbents for the isolation of organisms, enzymes localized onto the cell surface and the like.

Especially levansucrase expressed onto the cell surface is very useful to produce levan from sucrose and the process of the present invention can be used for the bioconversion efficiently.

We claim:

1. A method for associating foreign protein with a surface of a cell comprising:

providing a recombinant vector containing nucleic acid encoding the foreign protein fused to nucleic acid encoding a protein selected from the group consisting of ice nucleation protein (INP) and partial ice nucleation protein (partial INP) wherein INP includes N-terminal unique amino acids, a central repeating region and C-terminal unique amino acids, and partial INP includes N-terminal unique amino acids and C-terminal unique amino acids without a central repeating region;

transforming a gram negative bacterium with the recombinant vector to provide a transformant; and culturing the transformant to provide a fusion protein which includes the N-terminus of the foreign protein fused to one of the C-terminal unique amino acids of INP or partial INP.

2. A method for associating foreign protein with the surface of a cell according to claim 1, wherein the foreign protein is levansucrase.

3. A method for associating foreign protein with the surface of a cell according to claim 1 wherein a distance between the foreign protein and the surface of the cell can be adjusted by adjusting the length of the nucleic acid encoding the central repeating region of the complete INP protein.

4. A method for associating foreign protein with the surface of a cell according to claim 1 wherein INP or partial INP is derived from *Psuedomonas syringae* KCTC 1832.

5. A method for associating foreign protein with the surface of a cell according to claim 1 wherein the INP or partial INP includes a secretion signal sequence, a targeting signal sequence and a cell membrane binding sequence.

6. A method for associating foreign protein with the surface of a cell according to claim 1 wherein the nucleic acid encoding the C-terminal unique amino acids of INP or partial INP contains restriction sites for insertion of foreign genes.

7. A method for associating foreign protein with the surface of a cell according to claim 6 wherein the recombinant vector is made by:

providing a surface anchoring vector including the nucleic acid encoding the C-terminal unique amino acids of INP or partial INP and inserting the nucleic acid encoding the foreign protein at the location of the restriction sites.

8. A method for associating foreign protein with the surface of a cell according to claim 7 wherein the surface anchoring vector is pANC3.

9. A method for associating foreign protein with the surface of a cell according to claim 8, wherein the surface anchoring vector pANC3 is included in *E. coli* transformant KCTC 0326 BP (accession number: KCTC 0326 BP).

10. A method for associating foreign protein wit the surface of a cell according to claim 7, wherein the surface anchoring vector is pGINP21M.

11. A method for associating foreign protein with the surface of a cell according to claim 10, wherein the surface anchoring vector pGINP21M is included in *E. coli* transformant KCTC 0239BP (accession number: KCTC 0239 BP).

12. A method for associating foreign protein with the surface of a cell according to claim 1, wherein the recombinant vector is pANC3-CM2 which includes a surface anchoring vector pANC3 and a nucleic acid encoding the foreign protein CMCase.

13. A method for associating foreign protein with the surface of a cell according to claim 1, wherein the recombinant vector is pASCM1 which includes a surface anchoring vector pGINP21M and a nucleic acid encoding the foreign protein CMCase.

14. A method for associating foreign protein with the surface of a cell according to claim 1, wherein the recombinant vector is pASLP1 which includes a surface anchoring vector pGINP21M and a nucleic acid encoding the foreign protein lipase.

15. A method for associating foreign protein with the surface of a cell according to claim 1, wherein the recombinant vector is pASIg1 which includes a surface anchoring vector pGINP21M and a nucleic acid encoding the foreign protein humanized single chain Fv antibody.

16. A method for associating foreign protein wit the surface of a cell according to claim 1, wherein the recombinant vector is pSSTS109 which includes a surface anchoring vector pGINP21M and a nucleic acid encoding the foreign protein levansucrase.

17. A method for associating foreign protein with the surface of a cell according to claim 1, wherein the host cell is selected for the group consisting of *Escherichia coli,* Acetobacter sp., Pseudomonas sp., Xanthomanas sp., Erwinia sp., and Xymomonas sp.

18. A method for associating foreign protein with the surface of a cell according to claim 1, wherein the transformant is obtained by transforming *E. coli* JM109 with the pANC3-CM2recombinant vector.

19. A method for associating foreign protein with the surface of a cell according to claim 1, wherein the transformant is obtained by transforming *E. coli* JM109 with the pASCM1 recombinant vector (accession number: KCTC 0237 BP).

20. A method for associating foreign protein wit the surface of a cell according to claim 1, wherein the transformant is obtained by transforming *E. coli* JM109 with the pASLP1 recombinant vector.

21. A method for associating foreign protein wit the surface of a cell according to claim 1, wherein the transformant is obtained by transforming *E. coli* JM109 with the pASIg1 recombinant vector.

22. A method for associating foreign protein with the surface of a cell according to claim 1, wherein the transformant is obtained by transforming *E. coli* DH5α with the pSSTS109 recombinant vector (accession number: KCTC 0327 BP).

23. A method for associating ice nucleation protein (INP) with a surface of a cell comprising:

providing a recombinant vector containing nucleic acid encoding one protein selected from the group consisting of INP and partial INP, wherein the INP includes N-terminal unique amino acids, a central repeating region and C-terminal unique amino acids, and the partial INP comprises N-terminal unique amino acids and C-terminal unique amino acids without a central repeating region;

transforming a gram negative bacterium with the recombinant vector to provide a transformant; and culturing the transformant to provide INP or partial INP or both.

24. A method for associating INP with a surface of a cell according to claim 23, wherein the nucleic acid encoding the C-terminal unique amino acids of INP or partial INP contains restriction sites for insertion of foreign genes.

* * * * *